United States Patent

Wong et al.

[11] Patent Number: 5,090,804
[45] Date of Patent: Feb. 25, 1992

[54] APPARATUS AND METHOD FOR INSPECTION OF SURFACE QUALITY OF SMOOTH SURFACES

[75] Inventors: Andrew K. Wong; Mohamed S. Kamel; John T. King, all of Waterloo, Canada

[73] Assignee: Virtek Vision Intelligence Robotics Technologies Corporation, Waterloo, Canada

[21] Appl. No.: 459,750
[22] PCT Filed: Jul. 27, 1988
[86] PCT No.: PCT/US88/02706
 § 371 Date: Jan. 29, 1990
 § 102(e) Date: Jan. 29, 1990
[87] PCT Pub. No.: WO89/01146
 PCT Pub. Date: Feb. 9, 1989

[30] Foreign Application Priority Data

Jul. 30, 1987 [GB] United Kingdom ............... 8718073

[51] Int. Cl.⁵ ............................................. G01N 21/00
[52] U.S. Cl. .................................. 356/237; 356/446; 362/347
[58] Field of Search ............... 356/237, 429–431, 356/445, 446; 362/302, 347

[56] References Cited

U.S. PATENT DOCUMENTS

| | | | |
|---|---|---|---|
| 2,315,282 | 3/1943 | Snow | 356/446 |
| 3,588,492 | 6/1971 | Pollock | 362/347 |
| 3,977,792 | 8/1976 | Jumonji et al. | 356/445 |
| 4,245,913 | 1/1981 | Sarlos | 356/445 |
| 4,448,527 | 5/1984 | Milana | 250/225 |
| 4,630,276 | 12/1986 | Moran | 356/237 |
| 4,863,268 | 9/1989 | Clarke et al. | 356/237 |

FOREIGN PATENT DOCUMENTS

0142239 6/1988 Japan .................................. 356/237

Primary Examiner—Richard A. Rosenberger
Assistant Examiner—Hoa Pham
Attorney, Agent, or Firm—Daryl W. Schnurr

[57] ABSTRACT

A method and apparatus (2) for inspecting the surface quality of automotive parts (38) having smooth surfaces (44) utilizes a light source (4) and diffusing surface (6) contained in an opaque enclosure (8). The diffusing surface has a convex shape and is arranged relative to the light source to direct a gradient of light through the aperture (10) in the form of a beam. An object to be inspected is placed in the beam at a low angle relative to the inspection apparatus. All extraneous light is controlled and the beam is reflected off the object to an observer. The gradient in the reflective beam exposes any defects on the surface that are located on the beam and the location of the defects is noted. The inspection system and method can be used to inspect objects having surfaces that range from being highly reflective to lowly reflective. The curvature and location of the diffusing surface within the enclousre is adjustable. The size and location of the aperture is also adjustable. The apparatus and method is particularly suited to inspect body parts in the automotive industry. No pretreatment of the parts is required. The system can be used in a production line with the parts mounted on a conveyor system (40). The observer cab be the human eye (48) or a camera (46) or series of cameras. The system is readily adaptable to observation by machine vision.

35 Claims, 8 Drawing Sheets

APPARATUS AND METHOD FOR INSPECTION OF SURFACE QUALITY OF SMOOTH SURFACES

BACKGROUND OF THE INVENTION

1. Field of the Invention

This invention relates to an apparatus and method for inspecting the surface quality of objects having smooth surfaces, ranging from highly reflective to lowly reflective for defects. More particularly, this invention relates to an apparatus and method whereby parts with smooth surfaces, whether highly reflective or lowly reflective can be inspected by observing a beam of light that is reflected from the part.

2. Description of the Prior Art

The inspection of parts having smooth surfaces has been a long outstanding problem and is of particular importance to the automotive industry. It is known to use a special lighting arrangement in conjunction with pretreating the part with highlighting oil which improves the reflective property of the surface. Unfortunately, the use of the highlighting oil is disadvantageous because the oil has a mild toxicity and unnecessary time is expended in applying the oil and subsequently removing it after the inspection has been completed. This method of inspection is carried out at a station often referred to as the 'Green Room'. This room has special lighting and a special dolly is provided to hold the sample. The part to be inspected is cleaned and the highlighting oil is spread over the surface. The oil is usually allowed to settle for ten minutes and then an inspector moves about the sample looking for defects. This process does not lend itself to further adaptation for inspection through machine vision systems. Also, it is unsuitable for assembly line inspection. Since the inspection process takes a great deal of time, only a small portion of the total number of parts being produced can be inspected. If a defect is noted, the production line is stopped but, by that time, many parts containing the same defect usually have already been produced. It is not unusual for this type of inspection to take more than two hours for one part.

Figure 1:
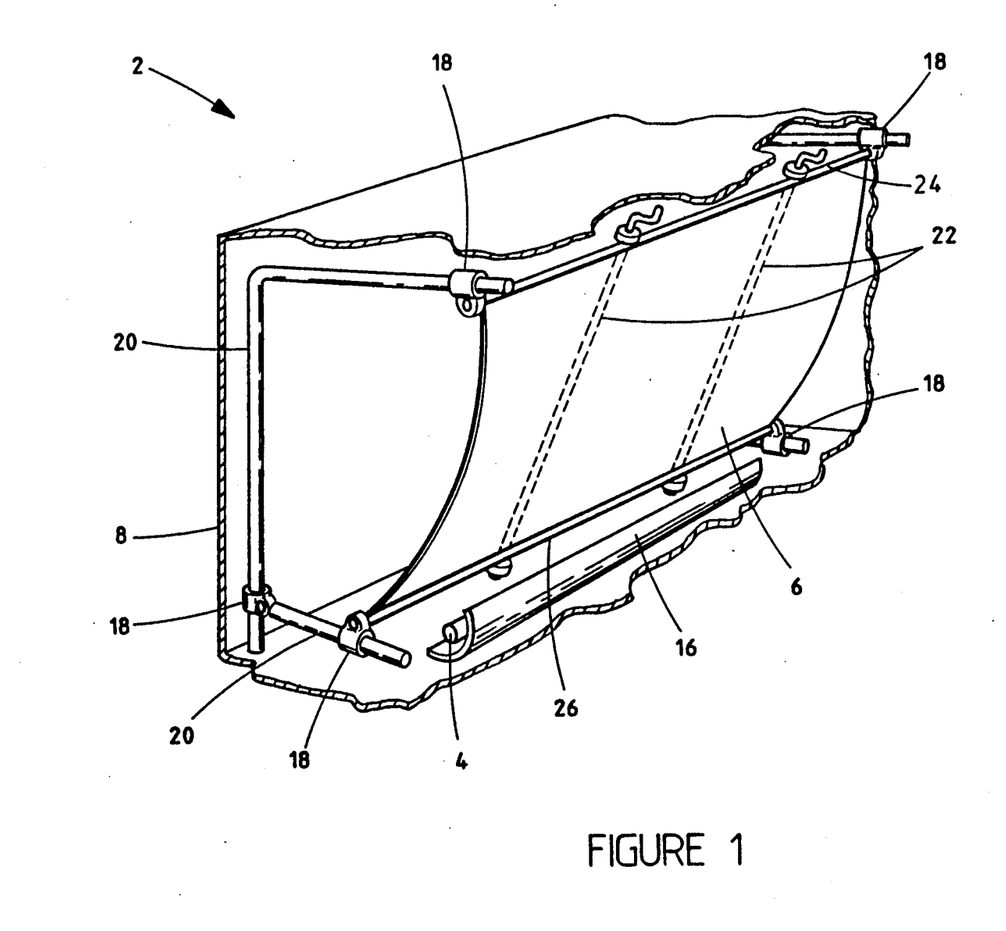
FIG. 1 is a partial perspective view of an inspection apparatus.
Figure 2:
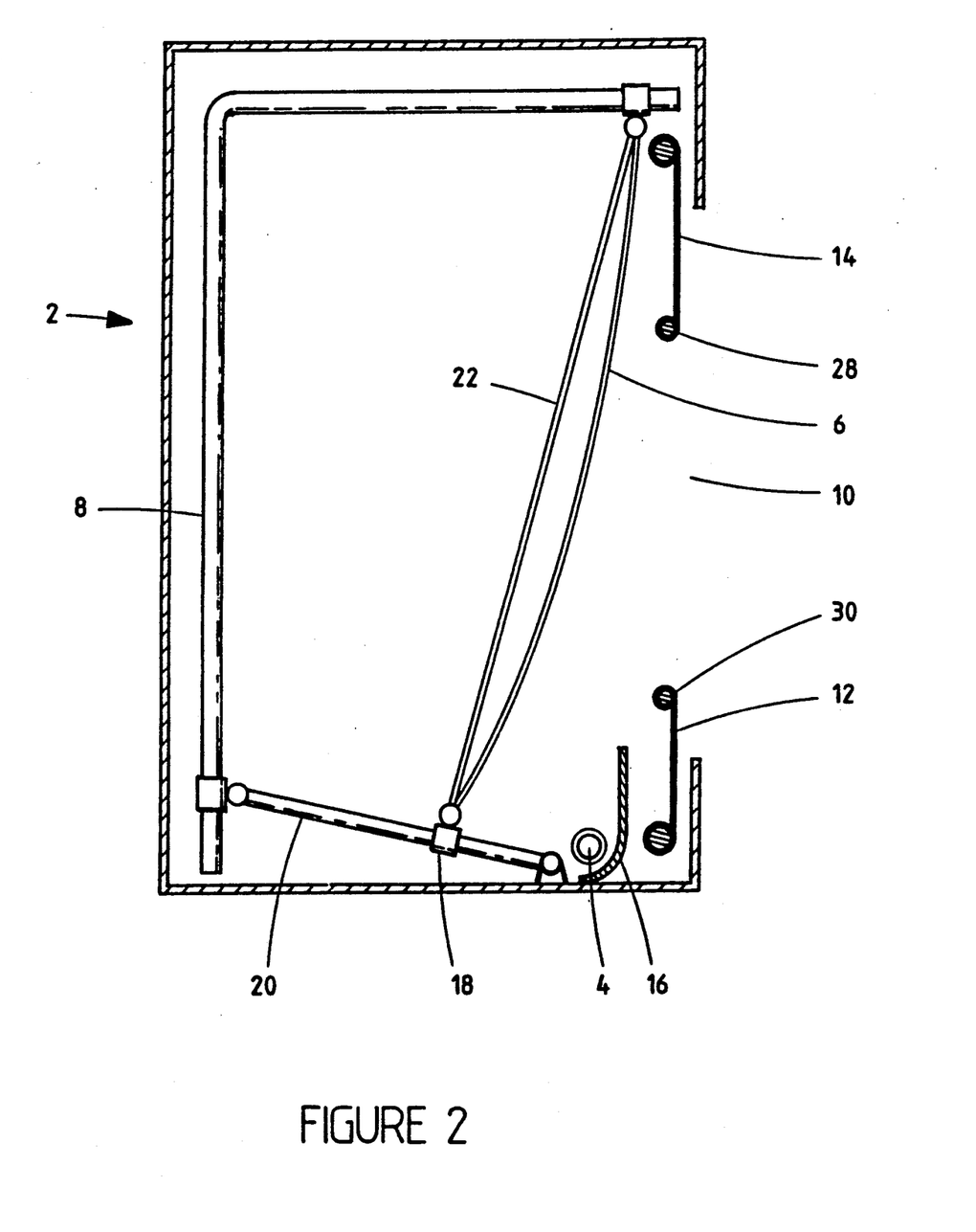
FIG. 2 is a schematic side view of the inspection apparatus of FIG. 1.

Another type of inspection system is described in U.S. Pat. No. 3,666,370 entitled "Strip Flatness Inspection Method", naming E. F. Seasholtz as inventor and issued on May 30, 1972. This patent describes the use of a diffused light source to inspect steel sheet or strip in a continuous processing line. The diffused light source can be a fluorescent bulb or bulbs mounted in a shallow rectangular box. The box is said to have a plurality of removable shutters for adjusting the height and/or thickness of a light slit which by means of a white translucent cover is transmitted in the form of a diffused light impinging on the strip being inspected and reflected to the eye of an observer (whether human or a camera). The slit and a plane of the surface being inspected are parallel to one another. This system has not replaced the 'Green Room' system of inspection, described above, in the automotive industry. Further, this system does not produce acceptable results for parts having lowly reflective surfaces or highly reflective surfaces when compared to the results achievable with the present invention. It should be noted that the translucent cover is shown in FIGS. 1 and 2 as being located at the front of the box and would therefore have the effect of scattering the light from the box in all directions, thereby destroying the effect of any gradient of intensity previously created in the light. The effect of placing the cover at the front of the box is essentially the same as if a flourescent lightbulb was placed at the front of the box.

With known inspection systems, especially for highly reflective surfaces, the angle of reflection within which an observer can detect defects is much too narrow and the area of inspection is much too small.

SUMMARY OF THE INVENTION

It is an object of the present invention to provide a surface inspection system for use with objects having smooth surfaces that range from being highly reflective to being lowly reflective and, from being highly curved to being flat, said system not requiring any surface preparation. It is a further object of the present invention to provide such a system using diffused light and a diffusing surface where the diffusing surface is located some distance behind the aperture and the diffused light and diffusing surface are arranged so that a gradient of light passes through the aperture, the light being directed on an object to be inspected.

An apparatus for inspecting the surface quality of objects having smooth surfaces for defects, where the type of surface ranges from highly reflective to lowly reflective, has a light source and diffusing surface. The light source and diffusing surface are contained in an opaque enclosure, the enclosure having an aperture through which some of the light can escape. The light source and diffusing surface are arranged to produce a gradient of light through the aperture. The diffusing surface is located some distance behind the aperture and the light emitted from the aperture is directed in the form of a beam. There are means for supporting a particular object to be inspected at a low angle in said beam so that said object reflects said beam away from said enclosure, while controlling an extraneous light. There are means to observe the reflected beam, the gradient in the reflected beam exposing any defects on said surface that are located in said beam of light so that the location of said defects can be noted.

A method of inspecting the surface quality of objects having smooth surfaces, ranging from highly reflective to lowly reflective uses a light source and diffusing surface contained in an opaque enclosure. The enclosure has an aperture through which light can escape. The diffusing surface is located some distance behind the aperture and the light emitted from the aperture is directed in the form of a beam. The method comprises arranging the light source and diffusing surface to produce a gradient of light through the aperture, placing an object to be inspected in a low angle in the beam of light emitted from the aperture so that the light is reflected away from said enclosure, controlling any extraneous light, observing said light as it is reflected from the object, noting the location of any defects in the object, moving the object and enclosure relative to one another to inspect other areas of the object if necessary or desired, noting the location of any defects for these other areas and repeating the observation steps as is necessary or desired to ultimately inspect the entire object.

DESCRIPTION OF A PREFERRED EMBODIMENT

Figure 3:
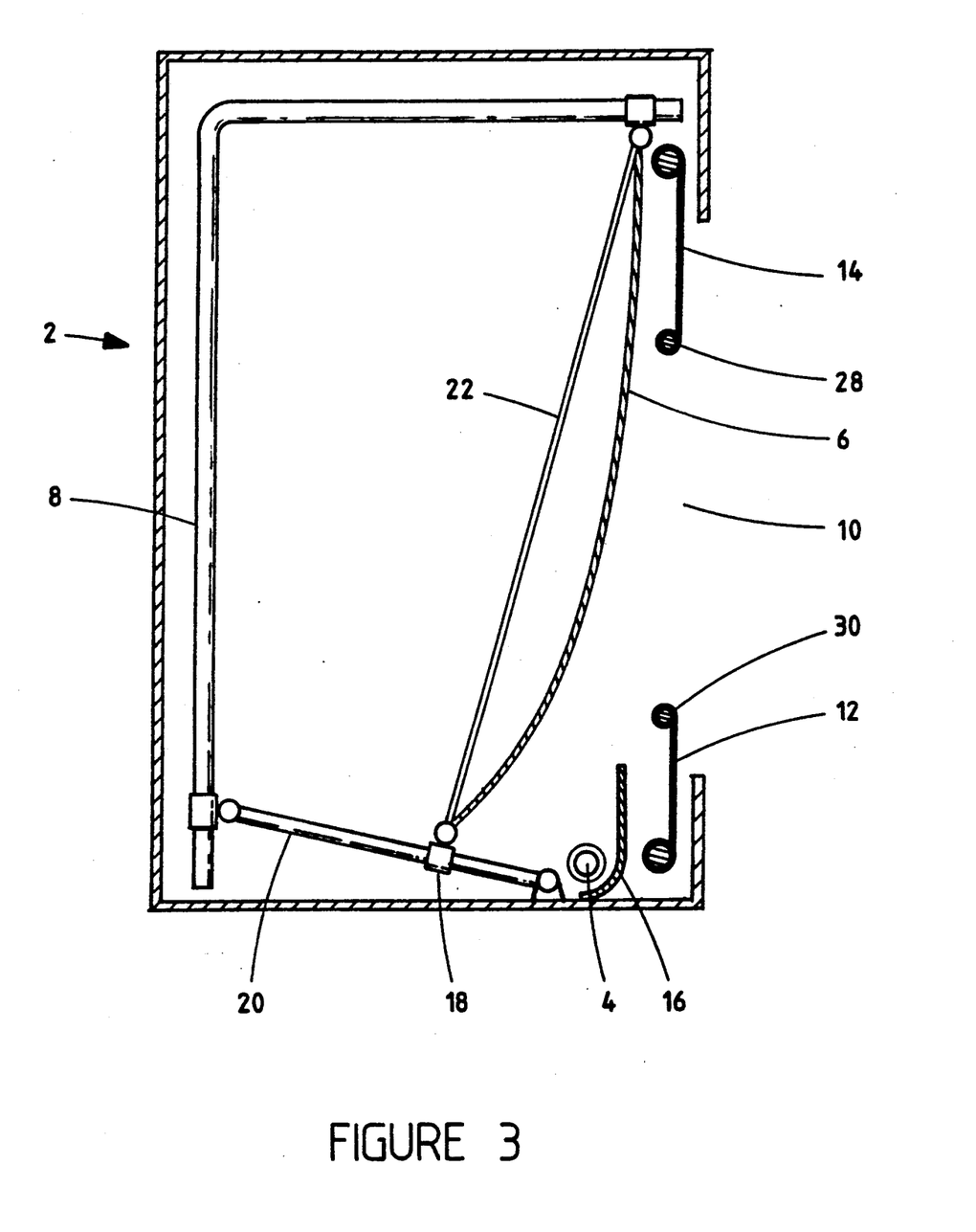
FIG. 3 is a partial schematic side view of the apparatus of FIG. 1 showing a diffusing surface with an increased curvature.

In FIGS. 1 and 2, there is shown an apparatus 2 for inspecting the surface quality of objects (not shown) having smooth surfaces for defects. The apparatus can be used to inspect types of smooth surfaces ranging from highly reflective to lowly reflective and can detect minute defects. The apparatus has a light source 4 and a diffusing surface 6. Both the light source 4 and the diffusing surface 6 are enclosed in an opaque enclosure 8, which is shown partially removed in FIGS. 1 and 2 for purposes of illustration. The enclosure has an aperture 10 through which some of the light can escape. The light source 4 and diffusing surface 6 are arranged to produce a gradient of light through the aperture 10. It should be noted that the diffusing surface 6 and the light source 4 are located some distance behind the aperture 10. The aperture has a rectangular shape and the size and location of the aperture are adjustable by opening or closing blinds 12, 14 which are located at the lower and upper edges respectively of the aperture 10. Preferably, the light source 4 is one or more lightbulbs and still more preferably is one or more fluorescent lightbulbs. The bulb 4 and the diffusing surface 6 are arranged so that light from the bulb reflects off the diffusing surface 6 and through the aperture 10. A shield 16 on the aperture side of the bulb 4 prevents any light from being emitted directly from the bulb 4 through the aperture 10. It should be noted that the diffusing surface 6 can be moved forward or backward within the enclosure 8 by suitably adjusting brackets 18 on elongated frame members 20. The curvature of the diffusing surface 6 can be adjusted by loosening or tightening connecting rods 22 to either increase or decrease the distance between an uppermost edge 24 and a lowermost edge 26 of the diffusing surface 6. In other words, the curvature of the diffusing surface 6 is adjustable. The curvature of the diffusing surface 6 shown in FIG. 3 is greater than the curvature of the diffusing surface 6 shown in FIG. 2.

Figure 4:
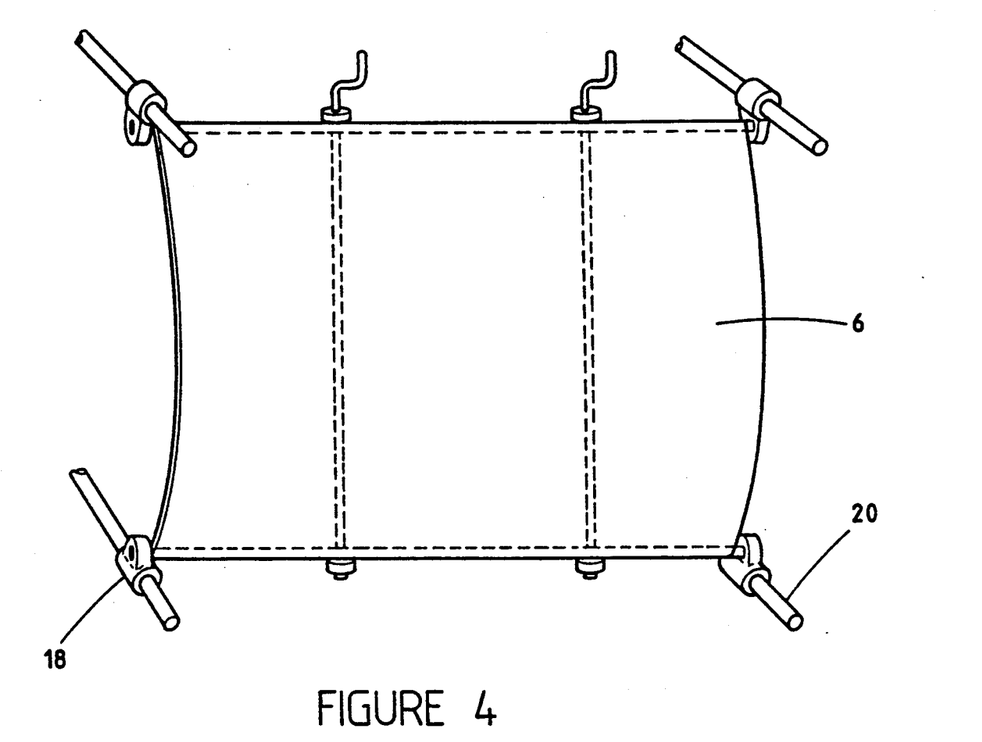
FIG. 4 is a partial perspective view of a front of the diffusing surface.
Figure 5:
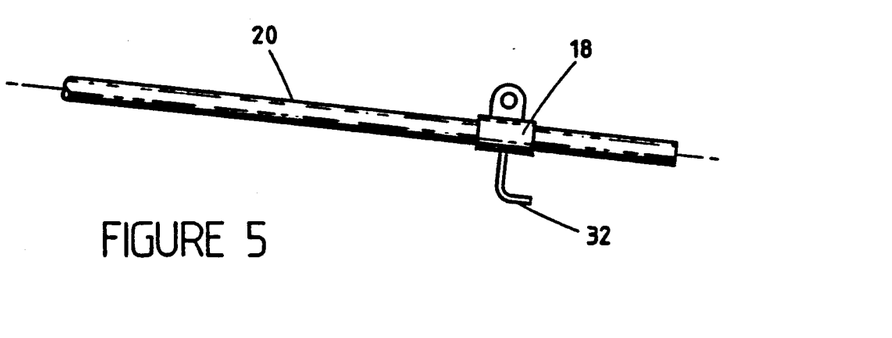
FIG. 5 is a side view of an elongated support member having a slidable bracket thereon.

A lower edge 28 of the blind 14 creates a transition zone in the gradient of light emitted from the aperture from low light to no light. The upper edge 30 of the blind 12 creates a transition zone in the gradient of light from the aperture from an area of bright light to an area of no light. The edges 28, 30 define the upper and lower edges of the aperture 10 and, as stated above, these edges are adjustable so that the size and location of the aperture can be adjusted. For example, if one wished to have an aperture in the form of a narrow slit located near the bottom of the enclosure 8, the blind 14 could be fully extended until it nearly meets the blind 12 at the location of the blind 12 shown in FIG. 2. Similarly, if one wished to have the aperture in the form of a narrow slit located near a top of the enclosure, the blind 12 could be extended until it nearly meets the present location of the blind 14 shown in FIG. 2. Thus, there are two transition zones created by the aperture 10, one along the edge 28 and one along the edge 30. In FIG. 4, there is shown a front view of the diffusing surface 6 supported by the slidable brackets 18 on elongated members 20. In FIG. 5, there is shown an elongated member 20 having a slidable bracket 18 located thereon. It can be seen that the slidable bracket 18 is adjustable by means of the handle 32.

Figure 6:
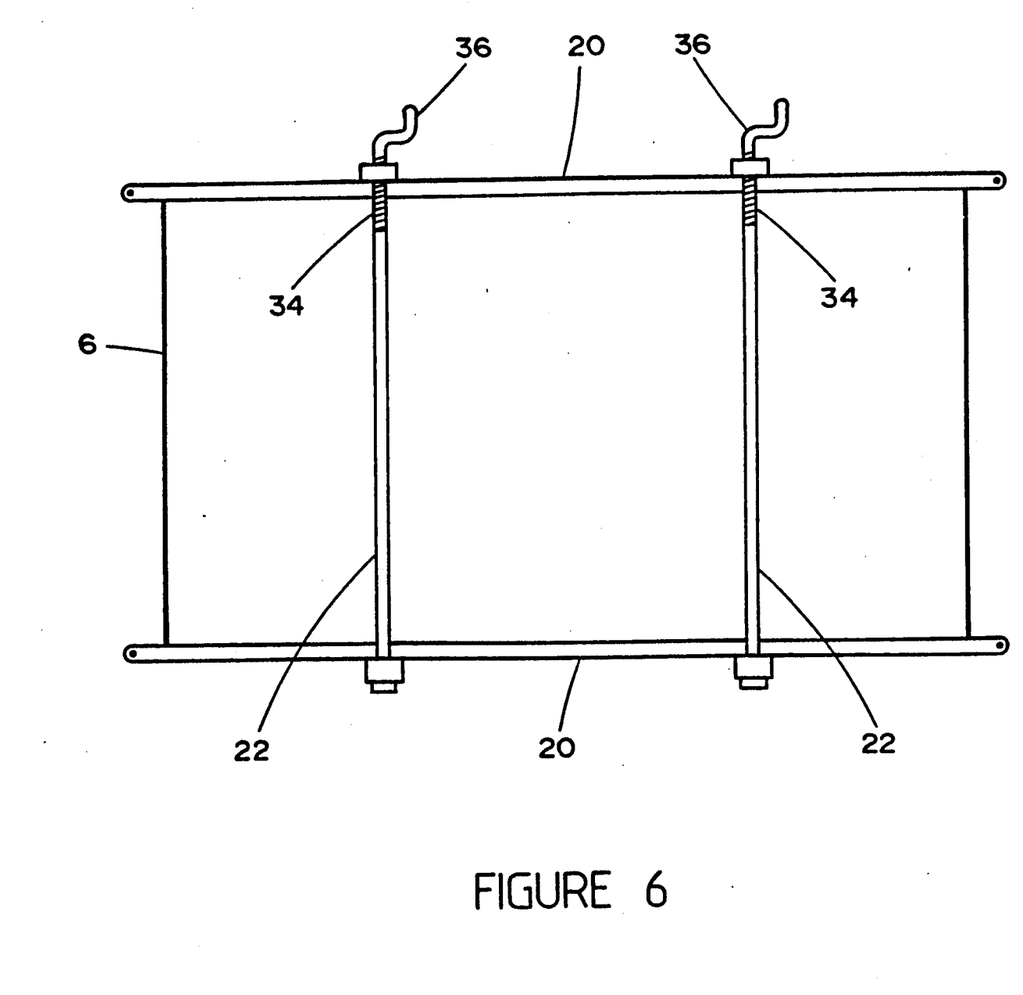
FIG. 6 is a rear view of the diffusing surface.
Figure 7:
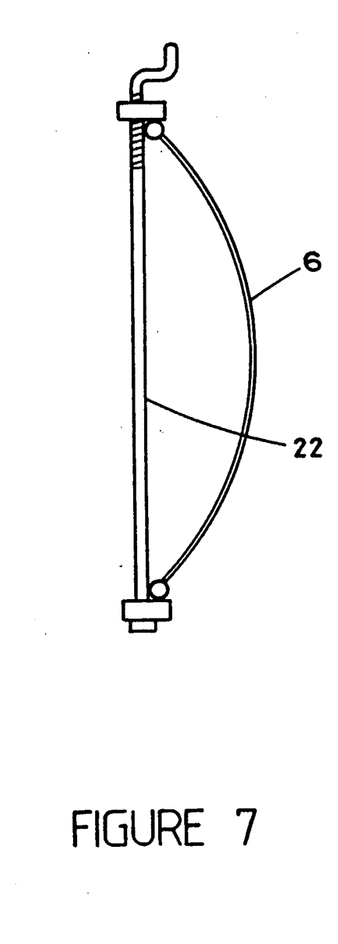
FIG. 7 is a side view of the diffusing surface shown in FIG. 6.

In FIGS. 6 and 7, there is shown a rear view and side view respectively of the diffusing screen 6. Connecting rods 22 connect the upper and lower frame members 20. The connecting rods 22 have screw threads 34 located thereon and handles 36 so that when the handles are turned in an appropriate direction the frame members 20 move either closer together or further apart, thereby increasing or decreasing the curvature of the diffusing surface 6.

Figure 8:
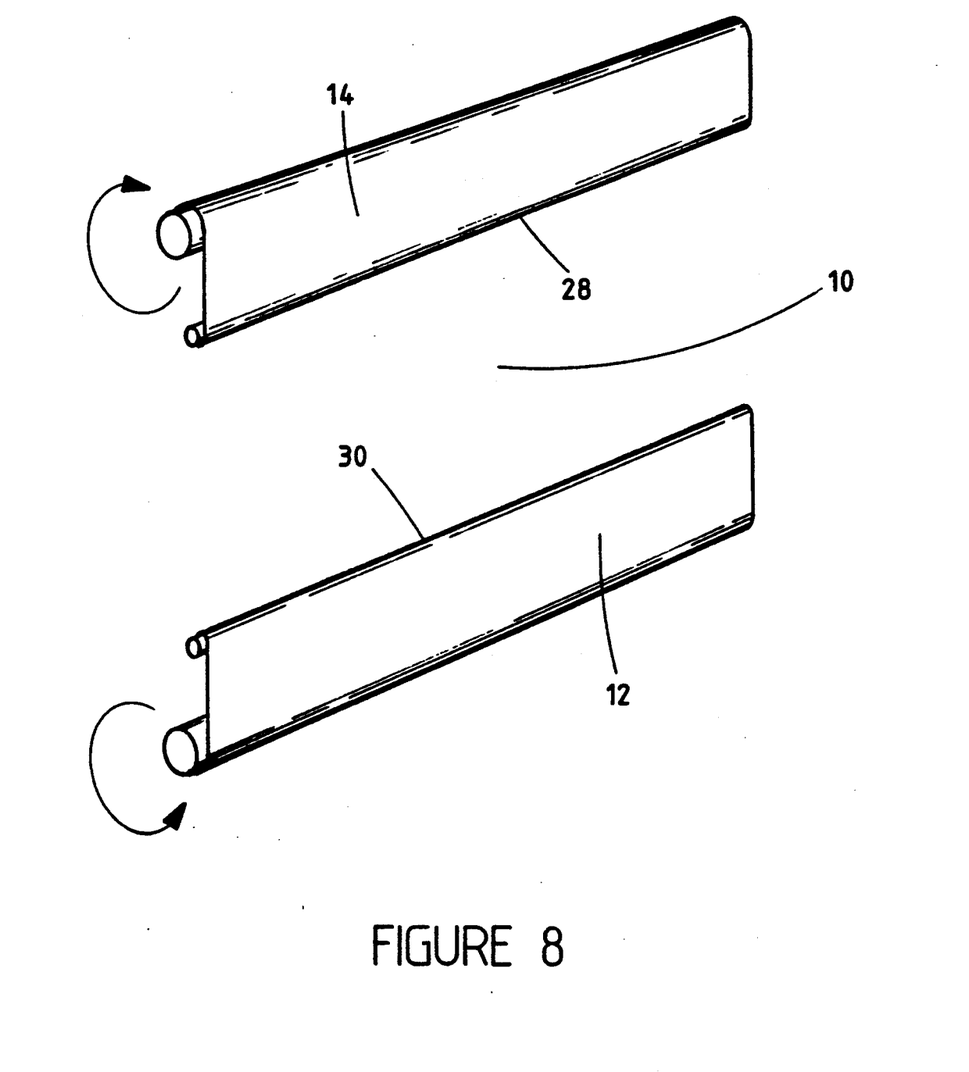
FIG. 8 is a partial perspective view of blinds used to block an aperture.

In FIG. 8, there is shown a perspective view of the blinds 12, 14 that form the lower and upper edges 30, 28 respectively of the aperture 10. While it is not shown in the drawings, the side edges of the blinds 12, 14 are mounted in suitable supports so that the blinds can be fixed at any desired level of the aperture.

Figure 9:
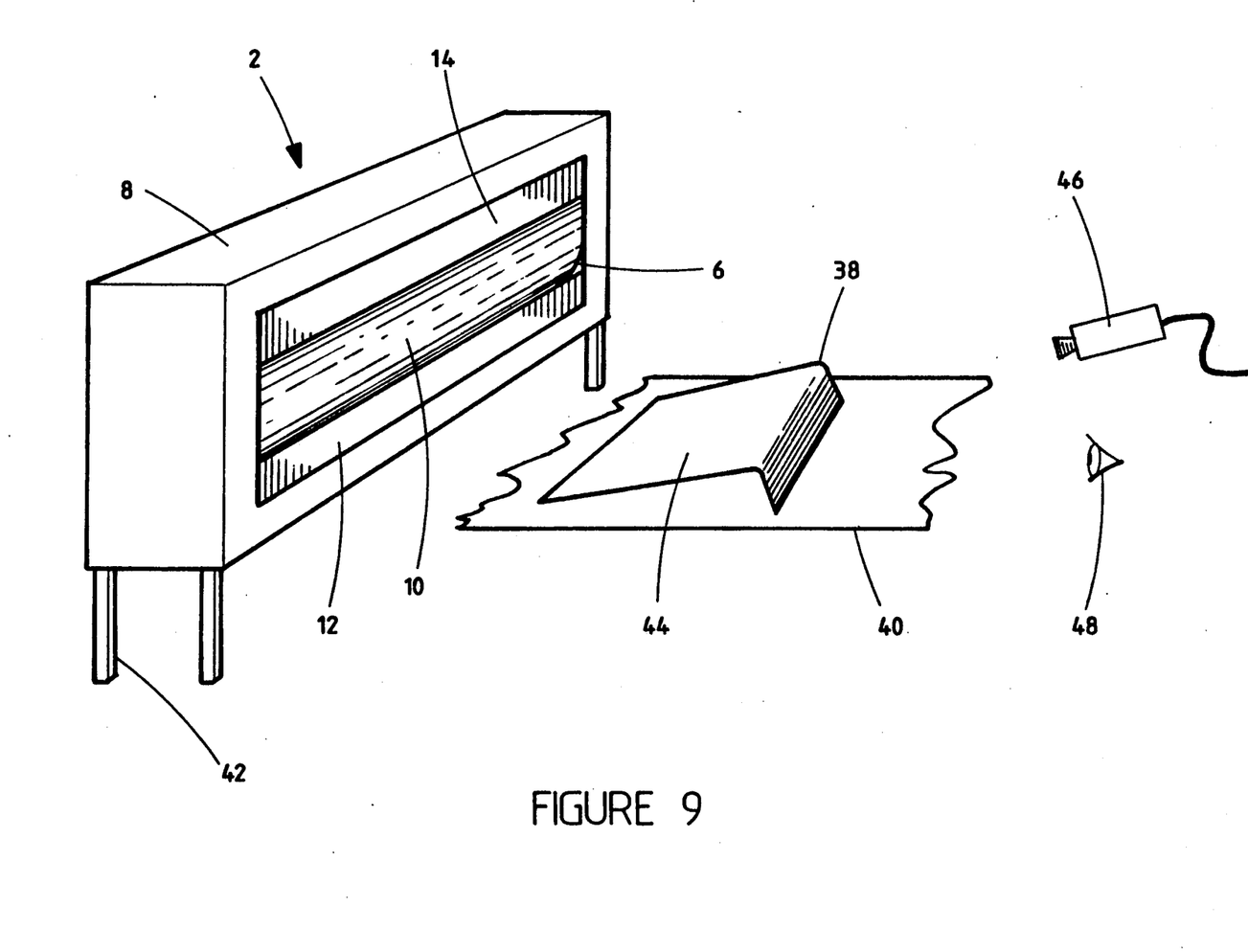
FIG. 9 is a perspective view of parts being fed toward an inspection apparatus.

In FIG. 9, the inspection apparatus 2 is shown being used to inspect an object 38 mounted on a movable support 40 (only part of which is shown). Preferably, the support 40 is a conveyor that moves the object 38 towards the apparatus 2 in a direction perpendicular to the aperture 10. If desired, the apparatus 2 could be located at an angle other than 90° relative to the conveyor 40.

While the apparatus 2 is shown as being supported by legs 42, the apparatus could be supported in any reasonable manner. It can be seen that the apparatus 2 is supported in such a way that the angle of the aperture 10 relative to the object 38 can be said to be a low angle. Preferably, the angle is equal to or less than 30°. The optimum angle will vary with the type of object being inspected. Light emitted from the aperture 10 and onto a surface 44 of the object 38 is reflected to an observer, which can either be a camera 46 or the human eye 48.

Figure 10:
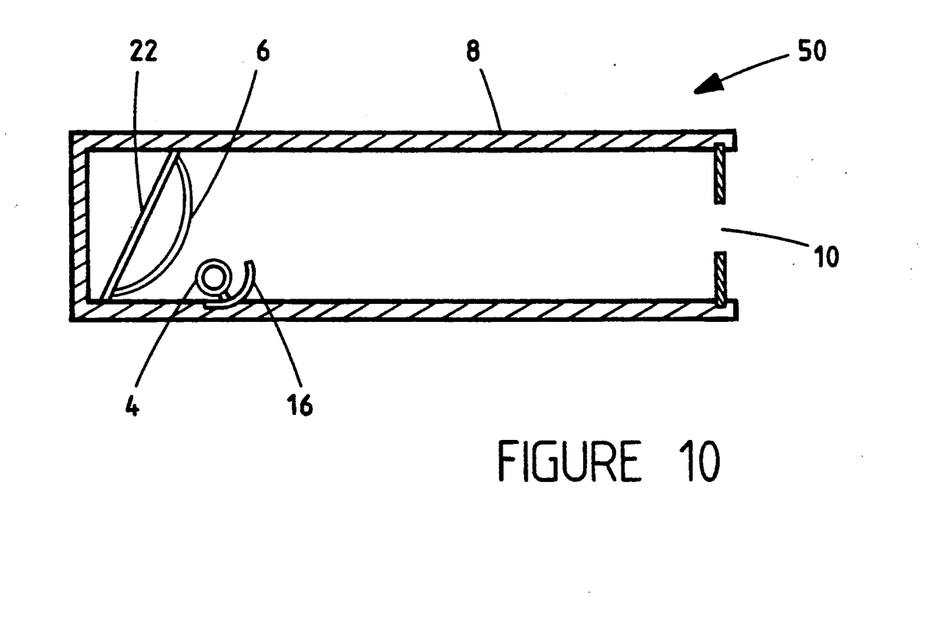
FIG. 10 is a sectional side view of a simplified embodiment of the inspection apparatus.

In FIG. 10, there is shown an inspection apparatus 50, which represents a further embodiment of the invention. The same reference numerals will be used in FIG. 10 for those components that are the same or similar to the components already described in FIG. 2. The apparatus 50 has an enclosure 8 and an aperture 10. The light source 4 is shielded from the aperture 10 by the shield 16. The light source emits light to a diffusing surface 6 which in turn emits the light through the aperture 10, which has a fixed size. No light passes directly from the light source 4 through the aperture 10. The diffusing surface 6 is adjustable in a manner similar to the apparatus 2, though the actual means of adjustment is not shown. It can be seen that the enclosure 8 is deep and that the light source 4 and diffusing surface 6 are located well back from the aperture 10.

Figure 11:
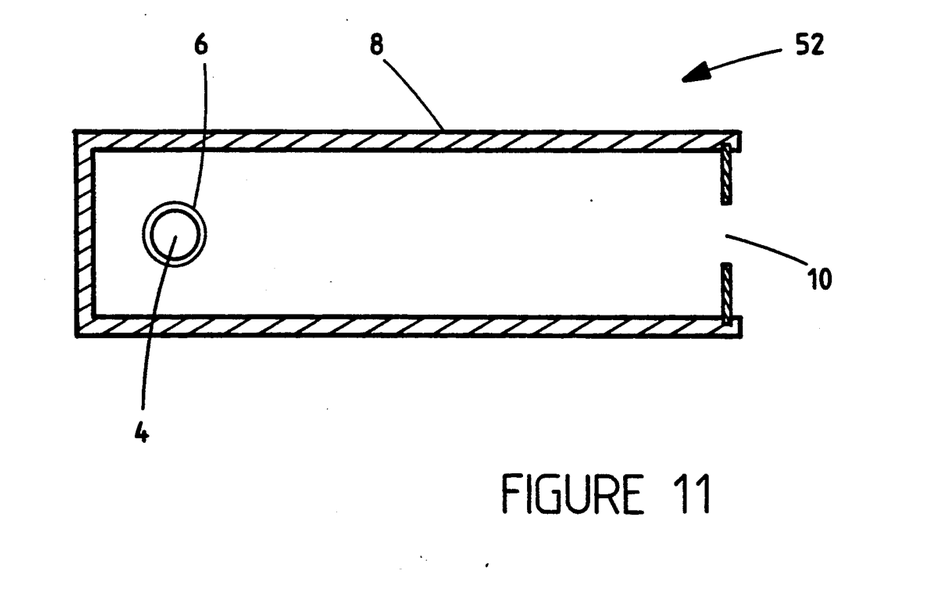
FIG. 11 is a sectional side view of a further embodiment of a more simplified inspection apparatus.

In FIG. 11, there is shown an inspection apparatus 52 which represents still a further embodiment of the invention. Again, the same reference numerals are used as for those used in FIG. 2 for those components that are the same or similar. The difference between the apparatus 50 and the apparatus 52 is that the apparatus 52 has a light source 4 which is a fluorescent bulb. The diffusing surface 6 is the actual surface of the bulb 4. Obviously, in the embodiments of the invention shown in FIGS. 2 and 10, when fluorescent bulbs are used, these bulbs of necessity also have a diffusing surface. However, in those embodiments, there is an extra diffusing surface 6. In the embodiment shown in FIG. 11, there is only one diffusing surface. While the embodiment shown in FIG. 11 is not a preferred embodiment as the light emitted by the lightbulb 4 will not be as diffused as the light emitted by, for example, the apparatus 50, the apparatus 52 will work well for specific applications. Neither the apparatus 50 nor the apparatus 52 are as versatile as the apparatus 2. However, for particular applications, for example, where the objects being inspected are always the same, a specific inspection apparatus can be designed to inspect those particular objects. The inspection apparatus can have a fixed aperture, and a fixed location of the diffusing surface. As with the apparatus 50, the bulb 4 and diffusing surface 6 in the apparatus 52 are located well back from the aperture 10 and the enclosure 8 is deep. Also, the aperture 10 is a relatively narrow slit that has a maximum size substantially equal to the size of the bulb 4. While the diffusing surface 6 is not adjustable in the apparatus 52, a fluorescent lightbulb having a larger or smaller diameter than the lightbulb shown could easily be placed into the enclosure 8. Also, while the aperture 10 of the apparatus 52 is fixed, the size of the aperture could easily be made adjustable.

While the light source and diffusing surface in the embodiments 50, 52 are a substantial distance back from the aperture compared to the location of the light source and diffusing surface of the apparatus 2, the location of the diffusing surface 6 is adjustable in the apparatus 2. Therefore, the diffusing surface could be moved to the back of the enclosure 8. Whether the light source 4 is located at the back or front of the enclosure 8 is not important when no light from the light source 4 is allowed to directly exit through the aperture 10.

The embodiments of the invention shown in FIGS. 10 and 11 are more specific versions of the more versatile apparatus 2 shown in FIG. 9. The apparatus 2 can be adjusted to produce the same results as the embodiments 50, 52. However, where there are a large number of objects to be inspected that are virtually the same, the optimum setting of the inspection apparatus can be readily determined theoretically based on the type and curvature of the surface or practically by conducting preliminary inspections using the inspection apparatus 2. Once the optimum setting of the apparatus 2 has been determined, a fixed setting, similar to the embodiments 50, 52 could be designed. The embodiments 50, 52, being much simpler than the embodiment 2, are also much less expensive to construct.

While other flat dark colours will be suitable, the inside surface of the enclosure 8, including the inside surface of the blinds 12, 14 preferably have a low reflective black colour. This can be accomplished by paint or a suitable covering. Also, great care must be taken so that no light is emitted from the enclosure 8 except through the aperture 10. In FIG. 2, the blinds 12, 14 are shown spaced apart from a front of the enclosure 8. This space is included for ease of illustration only. In actual practice, the space between the blinds 12, 14 and the front of the enclosure 8 is sealed off so that no light from the enclosure except through the aperture 10. Also, all extraneous light in a room where the apparatus is used is controlled, preferably by eliminating or at least minimizing such light. For certain types of objects and surfaces, it is not important that all of the extraneous light be eliminated but for other types of objects and surfaces, it becomes very important. Also, preferably, all surfaces in the room where the inspection takes place, except for the object being inspected, have a dull black finish or at least a dull dark finish.

While the object 38 shown in FIG. 9 is described as being movable relative to the apparatus 2, for some applications, it may be more beneficial not to move the object relative to the inspection apparatus. Also, for some applications, it may be desirable to reorient the object on the support in order to observe different areas of the part. When the reflected beam of light is observed by a camera, the camera can be connected to monitors (not shown) that are observed by the human eye. Alternatively, the camera can be connected to a computerized analysis system which will automatically produce a signal when a defect is discovered. While the diffusing surface can vary in material, colour and reflectivity depending upon the object to be observed, it is preferably made of flexible sheet metal that has a flat white surface. A flat white surface maximizes the scattering of the light when the light shines upon the surface. Preferably, the diffusing surface will always be convex but inspection systems can be designed where the diffusing surface is not convex. Obviously, the greater the degree of curvature in the diffusing surface, the greater the gradient of light that is created by the surface. Where the diffusing surface is relatively flat, the gradient of light will be created only slightly by the diffusing surface. In these circumstances, the gradient of light can be created mainly by an edge of the aperture.

In operation, an object to be inspected is moved toward the inspection apparatus. When an object, for example, an automotive part, has a highly reflective surface, the curvature of the diffusing surface is decreased, thereby decreasing the gradient of light emitted from the aperture. When inspecting highly reflective parts, the size of the aperture is increased. When inspecting parts having lowly reflective surfaces, the curvature of the diffusing surface is increased, thereby increasing the gradient of light emitted from the aperture. Further, when inspecting lowly reflective parts, the size of the aperture is decreased to a narrow slit.

The beam is all of the light that is emitted from the aperture and is obviously very wide when the aperture is very wide. Unlike previous systems that observe the mirror image of the light source in the object being inspected, the gradient of the present invention creates a shadow effect on the object. The shadow effect exposes the defect whether it be a dimple, a depression, a recoil, a roller mark, a projection or any other type of uneven surface. With the present invention the defect itself is observed. With previous inspection systems, a defect is discovered when the image of the light source (for example, a flourescent lightbulb in the 'Green Room') is distorted. For a projection, the side nearer the inspection apparatus is bright and the side away from the apparatus is darker. For a depression, the side nearer the inspection apparatus is darker and the side away from the apparatus is brighter. The shadow effect makes it much easier to adapt the present invention to machine vision than previous inspection systems. Also, the range of observation is much broader than with previous inspection systems. While the range varies with the type of object, a range of observation greater than 45° is not unusual.

The diffusing surface is always located behind the aperture so that the light emitted from the aperture is directed in the form of a beam. The location of defects can be noted in many ways. For example, where the observer is the human eye, actual written or typed notes can be made. Where a computer analysis system is connected to a camera or series of cameras, the location of any defects in the object can be noted by printed output from the system. For example, a graph plotting vertical distance up the screen against light intensity from the aperture can be produced, the graph depicting a straight line or curve when no defects are present and showing a blip in the straight line or smooth curve when a defect is present. The blip is caused by a rapid change in light intensity where the defect is located.

Numerous variations, within the scope of the attached claims, can be made in the apparatus or method of carrying out the present invention. For example, the inspection apparatus can be placed at an angle relative to the movement of the support means or conveyor carrying the objects to be inspected towards the apparatus. As long as one component of the direction of movement of the objects is perpendicular to the aperture (i.e. parallel to the beam of light) that will be sufficient. In other words, in the relative position of the enclosure and the object shown in FIG. 9, the object can be moved in any direction except for movement parallel to said slit across a front of the enclosure. Also, the objects could be moved in the opposite direction, from a location very close to the inspection apparatus to a location further away from the inspection apparatus. Further, the size and shape of the aperture as well as the variation in the curvature of the diffusing surface 6 could be accomplished in many different ways. While the objects to be inspected can vary, they will often be automotive body parts.

We claim:

1. An apparatus for inspecting the surface quality of objects having smooth surfaces for defects, where the type of surfaces range from highly reflective to lowly reflective, said apparatus comprising a light source and diffusing surface, the light source and diffusing surface being contained in an opaque enclosure, said enclosure having an aperture through which some of the light can escape, the light source and diffusing surface being arranged to produce a gradient of light through the aperture, the diffusing surface being located some distance behind the aperture and the light emitted from the aperture being directed in the form of a beam, with means for supporting a particular object to be inspected at a low angle in said beam so that said object reflects said beam away from said enclosures, while controlling any extraneous light, with means to observe the reflected beam, the gradient in the reflected beam exposing any defects on the surface of said object that are located in said beam of light so that the location of said defects can be noted.

2. An apparatus as claimed in claim 1 wherein the light source within the enclosure is created by at least one lightbulb, the at least one lightbulb and the diffusing surface being arranged so that light from the at least one lightbulb reflects off the diffusing surface and through the aperture, said diffusing surface having a curvature, there being no light emitted directly from the at least one lightbulb through the aperture.

3. An apparatus as claimed in claim 2 wherein the curvature of the diffusing surface is adjustable.

4. An apparatus as claimed in claim 3 wherein the aperture is adjustable in size.

5. An apparatus as claimed in claim 4 wherein the aperture has a rectangular shape.

6. An apparatus as claimed in claim 4 wherein the aperture has an edge that creates at least one transition zone in the gradient of light from light to no light.

7. An apparatus as claimed in claim 6 wherein the aperture creates two transition zones.

8. An apparatus as claimed in claim 7 wherein one transition zone is from bright light to no light and the other transition zone is from low light to no light.

9. An apparatus as claimed in any one of claims 2, 3 or 4 wherein the bulbs are fluorescent bulbs.

10. An apparatus as claimed in claim 4 wherein the location of the aperture is adjustable.

11. An apparatus as claimed in any one claims 1, 2 or 3 wherein the diffusing surface is located a substantial distance behind the aperture.

12. An apparatus as claimed in any one of claims 1, 2 or 3 wherein the object being inspected is located on a support that is movable relative to the apparatus.

13. An apparatus as claimed in claim 12 wherein the support for the object enables the object to be reoriented relative to the apparatus.

14. An apparatus as claimed in any one of claims 1, 2 or 3 wherein an inside surface of the enclosure has a dull black colour.

15. An apparatus as claimed in any one of claims 1, 2 or 3 wherein all extraneous light is eliminated.

16. An apparatus as claimed in any one of claims 1, 2 or 3 wherein the means to observe the light is the human eye.

17. An apparatus as claimed in any one of claims 1, 2 or 3 wherein the means to observe the reflected light is one or more cameras, said cameras being connected to monitors that are observed by the human eye.

18. An apparatus as claimed in any one of claims 1, 2 or 3 wherein the means to observe the reflected light is one or more cameras that are connected to a computerized analysis system.

19. An apparatus as claimed in claim 3 wherein the gradient of the light increases as the curvature of the diffusing surface increases.

20. An apparatus as claimed in any one of claims 2, 3 or 4 wherein the gradient of light is created only slightly by the diffusing surface and mainly by an edge of the aperture.

21. An apparatus as claimed in any one of claims 1, 2 or 3 wherein the size and location of the aperture is fixed.

22. An apparatus as claimed in claim 2 wherein the diffusing surface has a dull white finish.

23. An apparatus as claimed in any one of claims 2 or 4 wherein the angle of the aperture is adjustable.

24. An apparatus as claimed in claim 2 wherein the angle of the diffusing surface is adjustable relative to the aperture.

25. An apparatus as claimed in any one of claims 2 or 4 wherein the enclosure and object being inspected are movable relative to one another.

26. An apparatus as claimed in any one of claims 1 or 2 wherein the curvature of the diffusing surface is fixed.

27. An apparatus as claimed in claim 1 wherein the light source is a fluorescent lightbulb and the diffusing surface is a surface of the fluorescent bulb, the enclosure being deep and the bulb being located in the enclosure well back from the aperture, the aperture being a narrow slit that has a maximum size substantially equal to the diameter of the bulb.

28. A method of inspecting the surface quality of objects having smooth surfaces, ranging from highly reflective to lowly reflective, using a light source and a diffusing surface contained in an opaque enclosure, said enclosure having an aperture through which light can escape, the diffusing surface being located some distance behind the aperture and the light emitted from the aperture being directed in the form of a beam, said method comprising arranging the light source and diffusing surface to produce a gradient of light through the aperture, placing an object to be inspected at a low angle in the beam of light emitted from the aperture so that said light is reflected away from said enclosure, controlling any extraneous light, observing said light as it is reflected from the object, noting the location of any defects in the object, moving the object and enclosure relative to one another to inspect other areas of the object if necessary or desired, noting the location of any defects for these other areas and repeating the observation steps as is necessary or desired to ultimately inspect the entire object.

29. A method as claimed in claim 28 wherein the light source is a fluorescent lightbulb and the curvature of the diffusing surface is adjustable, the size of the aperture also being adjustable, said method comprising the steps of decreasing the curvature of the diffusing surface when inspecting objects having highly reflective surfaces, thereby decreasing the gradient of light emitting from the aperture, and increasing the curvature of the diffusing surface when inspecting objects having lowly reflective surfaces, thereby increasing the gradient of light emitting from the aperture.

30. A method as claimed in claim 29 including the steps of increasing the size of the aperture when inspecting objects having highly reflective surfaces and decreasing the size of the aperture to a relatively narrow slit when inspecting objects having lowly reflective surfaces.

31. A method as claimed in any one of claims 28, 29 or 30 including the step of moving the object and enclosure relative to one another during the inspection.

32. A method as claimed in any one of claims 28, 29 or 30 including the step of reorienting the object relative to the enclosure to inspect different areas of the object.

33. A method as claimed in any one of claims 28, 29 or 30 including the step of moving the object and enclosure relative to one another during the inspection in a direction that has one component parallel to said beam.

34. A method as claimed in claim 28 wherein the light source is a flourescent lightbulb, the gradient of light is adjustable and the aperture is adjustable, said method comprising the steps of decreasing the gradient of light when inspecting objects having highly reflective surfaces and increasing the gradient of light when inspecting objects having lowly reflective surfaces.

35. A method as claimed in claim 34 including the steps of increasing the size of the aperture when inspecting objects having highly reflective surfaces and decreasing the size of the aperture to a relatively narrow slit when inspecting objects having lowly reflective surfaces.

* * * * *